United States Patent
Sato et al.

(10) Patent No.: US 12,083,149 B2
(45) Date of Patent: Sep. 10, 2024

(54) AMELIORATION AND TREATMENT OF CHRONIC LUNG DISEASE USING PLURIPOTENT STEM CELLS

(71) Applicant: TOHOKU UNIVERSITY, Sendai (JP)

(72) Inventors: Yoshiaki Sato, Nagoya (JP); Toshihiko Suzuki, Nagoya (JP); Shinobu Shimizu, Nagoya (JP); Masaaki Mizuno, Nagoya (JP); Masahiro Hayakawa, Nagoya (JP); Mari Dezawa, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 331 days.

(21) Appl. No.: 16/322,781

(22) PCT Filed: Aug. 3, 2017

(86) PCT No.: PCT/JP2017/028323
§ 371 (c)(1),
(2) Date: Feb. 1, 2019

(87) PCT Pub. No.: WO2018/025973
PCT Pub. Date: Feb. 8, 2018

(65) Prior Publication Data
US 2019/0240262 A1  Aug. 8, 2019

(30) Foreign Application Priority Data
Aug. 3, 2016 (JP) .................. 2016-153263

(51) Int. Cl.
A61K 35/545 (2015.01)
A61P 11/00 (2006.01)

(52) U.S. Cl.
CPC ............ *A61K 35/545* (2013.01); *A61P 11/00* (2018.01)

(58) Field of Classification Search
None
See application file for complete search history.

(56) References Cited

U.S. PATENT DOCUMENTS

| | | | |
|---|---|---|---|
| 2012/0244129 A1 * | 9/2012 | Dezawa | C12N 5/0605 424/93.7 |
| 2016/0082048 A1 | 3/2016 | Yoshida et al. | |
| 2017/0258840 A1 | 9/2017 | Mitsialis et al. | |

FOREIGN PATENT DOCUMENTS

| | | | | |
|---|---|---|---|---|
| EP | 2 886 123 A1 | 6/2015 | | |
| EP | 2 683 389 B1 | 5/2017 | | |
| WO | WO-2008036374 A2 * | 3/2008 | ............. | A61K 35/28 |
| WO | WO-2011007900 A1 * | 1/2011 | ............. | A61K 35/12 |

OTHER PUBLICATIONS

Kuroda, Y., Wakao, S., Kitada, M. et al. Isolation, culture and evaluation of multilineage-differentiating stress-enduring (Muse) cells. Nat Protoc 8, 1391-1415 (2013). (Year: 2013).*

Miki T, Lehmann T, Cai H, Stolz DB, Strom SC. Stem cell characteristics of amniotic epithelial cells. Stem Cells. Nov. 2005-Dec. 23(10):1549-59. (Year: 2005).*

Nazarov I, Lee JW, Soupene E, Etemad S, Knapik D, Green W, Bashkirova E, Fang X, Matthay MA, Kuypers FA, Serikov VB. Multipotent stromal stem cells from human placenta demonstrate high therapeutic potential. Stem Cells Transl Med. May 2012;1(5):359-72. (Year: 2012).*

Moodley Y, Ilancheran S, Samuel C, Vaghjiani V, Atienza D, Williams ED, Jenkin G, Wallace E, Trounson A, Manuelpillai U. Human amnion epithelial cell transplantation abrogates lung fibrosis and augments repair. Am J Respir Crit Care Med. Sep. 1, 2010;182(5):643-51. (Year: 2010).*

Chang YS, Choi SJ, Sung DK, Kim SY, Oh W, Yang YS, Park WS. Intratracheal transplantation of human umbilical cord blood-derived mesenchymal stem cells dose-dependently attenuates hyperoxia-induced lung injury in neonatal rats. Cell Transplant. 2011;20(11-12):1843-54. (Year: 2011).*

Weiss DJ, Bertoncello I, Borok Z, et al. Stem cells and cell therapies in lung biology and lung diseases. Proc Am Thorac Soc. 2011;8(3):223-272. (Year: 2011).*

Lee JW, Rocco PR, Pelosi P. Mesenchymal stem cell therapy for acute respiratory distress syndrome: a light at the end of the tunnel? Anesthesiology. Feb. 2015;122(2):238-40. (Year: 2015).*

Aslam et al.Am J Respir Crit Care Med vol. 180. pp 1122-1130 (Year: 2009).*

Hayes Anesthesiology 122:363-73 (Year: 2015).*

Uchida et al J Am Soc Nephrol 28: 2946-2960 (Year: 2017).*

Dezawa Cell Transplantation, vol. 25, pp. 849-861 (Year: 2016).*

International Search Report issued Sep. 28. 2017 in PCT/JP2017/028323 (submitting English translation only), 1 page.

Van Haaften, T., et al., "Airway Delivery of Mesenchymal Stem Cells Prevents Arrested Alveolar Growth in Neonatal Lung Injury in Rats", American Journal of Respiratory and Critical Care Medicine, vol. 180, Aug. 27, 2009, pp. 1131-1142.

Ying-Wei Lan, et al., "Hypoxia-preconditioned mesenchymal stem cells attenuate bleomycin-induced pulmonary fibrosis," Stem Cell Research & Therapy, vol. 6, No. 97, 2015, pp. 1-17.

(Continued)

*Primary Examiner* — Anoop K Singh
(74) *Attorney, Agent, or Firm* — Oblon, McClelland, Maier & Neustadt, L.L.P.

(57) ABSTRACT

The purpose of the present invention is to provide a novel medical use of pluripotent stem cells (Muse cells) in the regenerative medicine area. Provided are a cell preparation and a medicinal composition for ameliorating and treating chronic lung disease in newborns, said cell preparation and medicinal composition comprising SSEA-3-positive pluripotent stem cells isolated from a mesenchymal tissue in a living body or cultured mesenchymal cells. The cell preparation according to the present invention is based on a mechanism whereby the aforesaid disease is ameliorated and treated by administering Muse cells to a subject suffering from the disease and engrafting the cells in lung tissues.

6 Claims, 9 Drawing Sheets

(56) References Cited

OTHER PUBLICATIONS

Shohei Wakao, et al., "Muse Cells, a Novel Type of Non-tumorigenic Pluripotent Stem Cells, that Reside in Human Mesenchymal Tissues," Spinal Surgery, vol. 28, No. 1, Apr. 2014, pp. 17-23 (with English Abstract).

Yunosuke Ogawa, "2. Concept of chronic lung disease in preterm infants," Journal of Japanese Society of Pediatric Pulmonology, vol. 11, No. 1, 2000, p. 51 (with English Abstract).

U.S. Office Action issued on Jul. 9, 2021 in U.S. Appl. No. 16/322,725.

* cited by examiner

FIG. 2
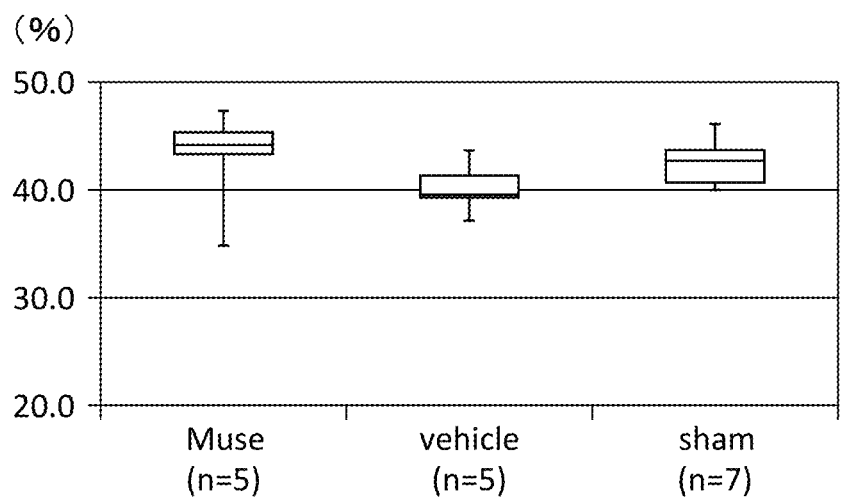
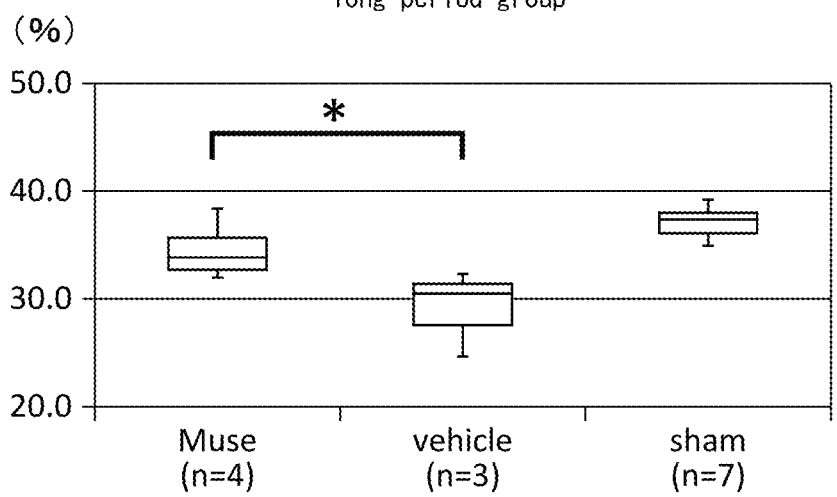

FIG. 6
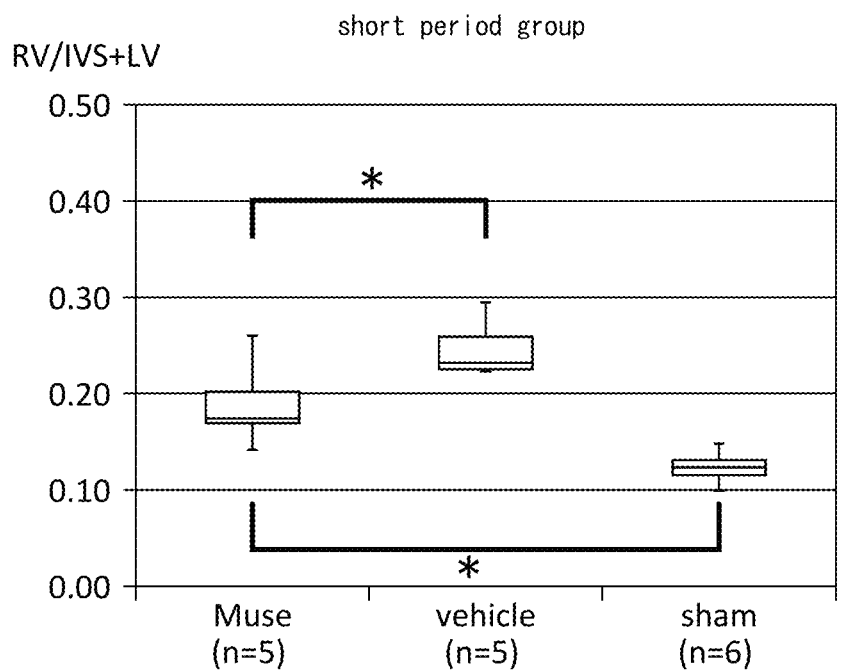
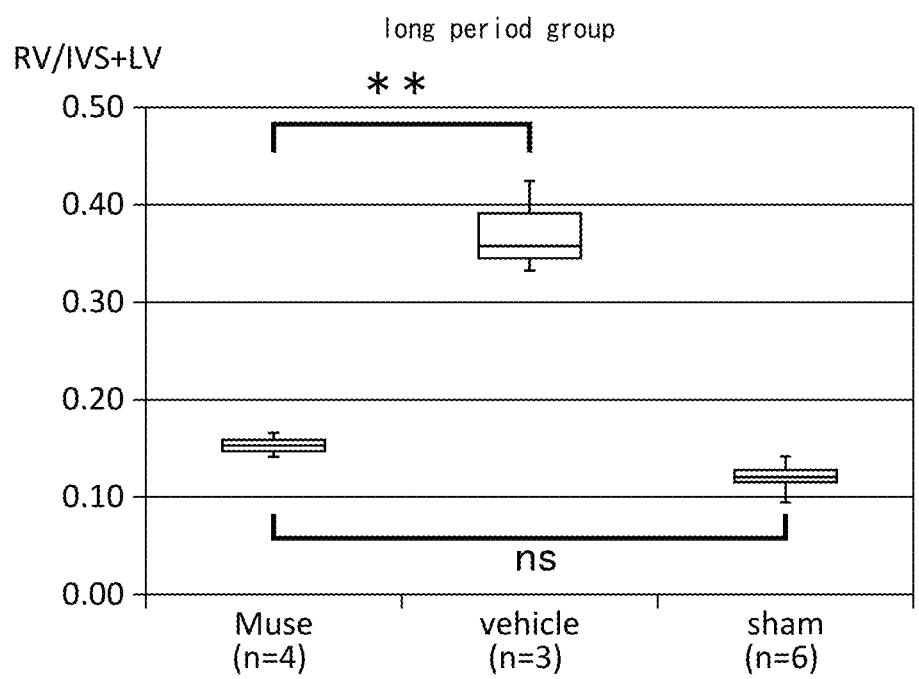

FIG. 8
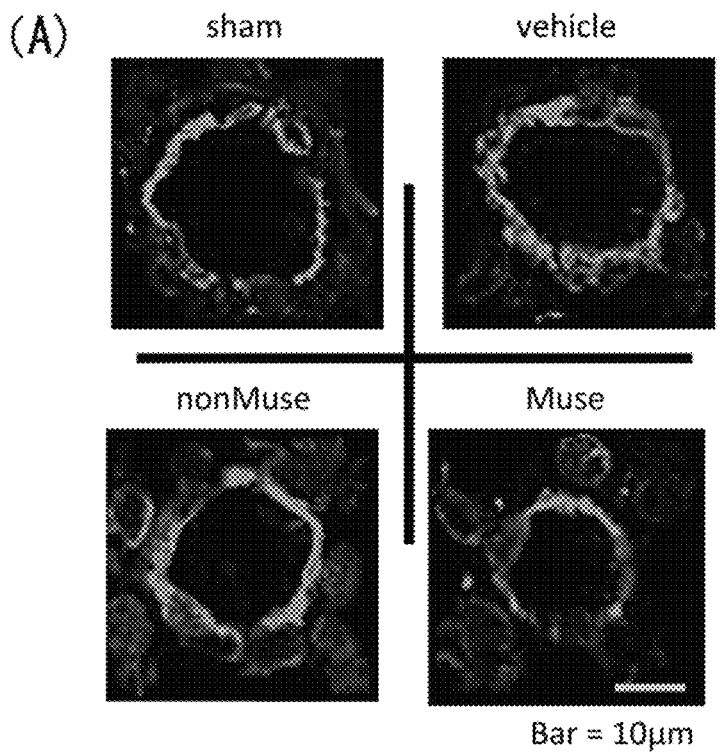
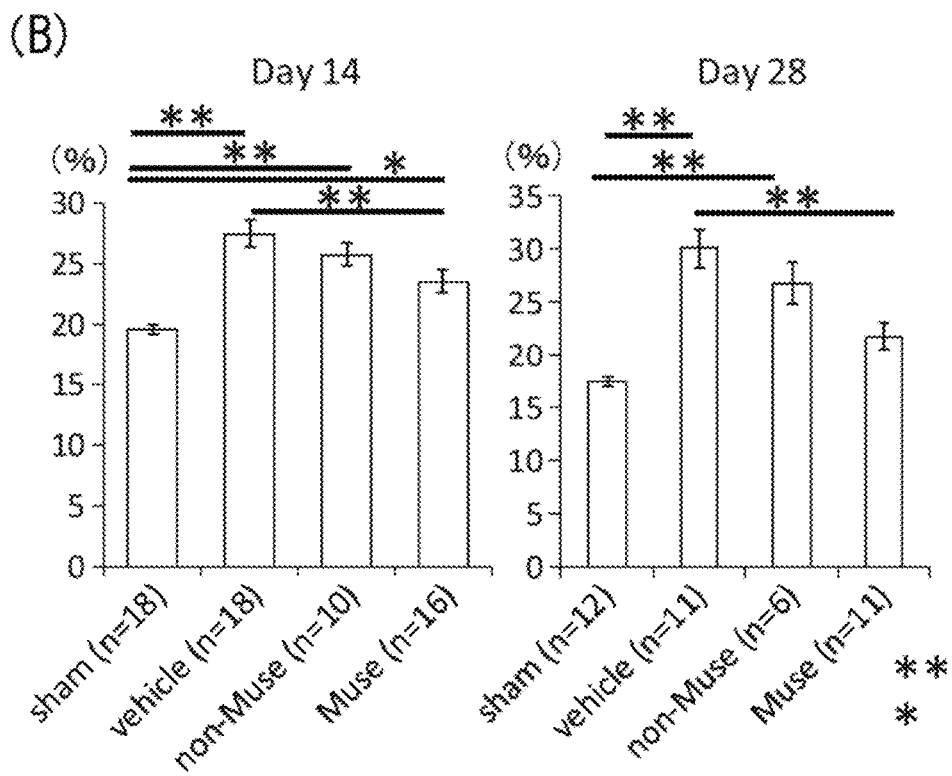

FIG. 9
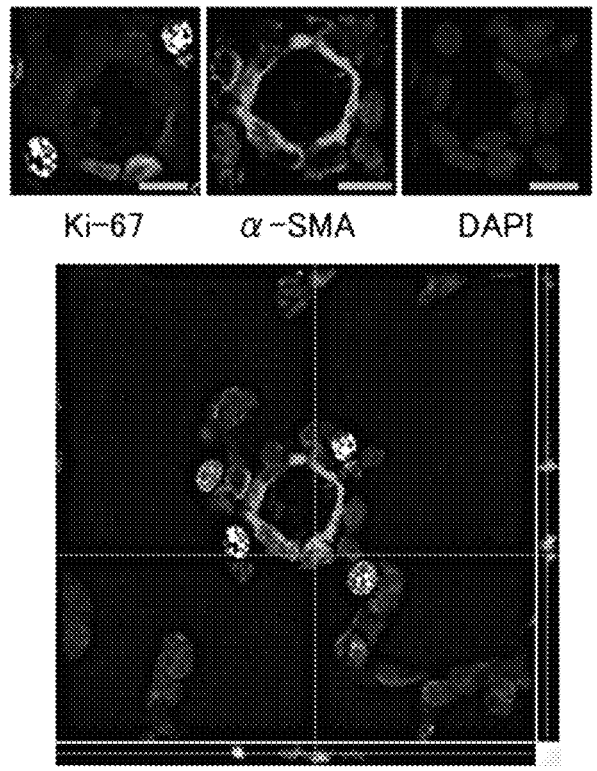
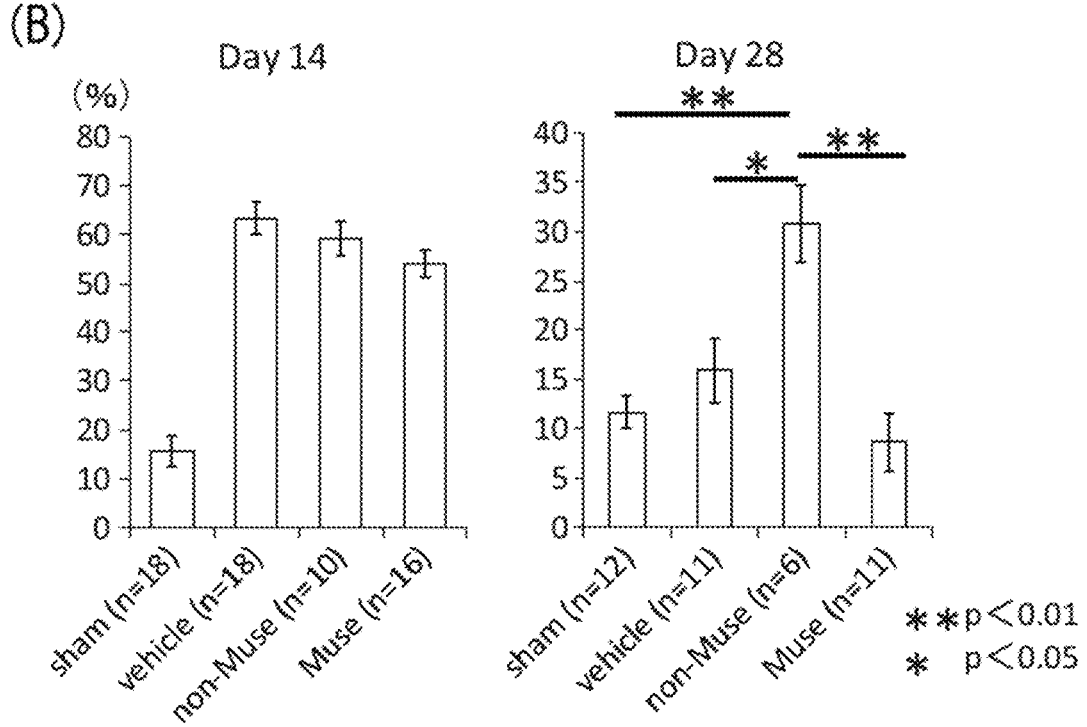

AMELIORATION AND TREATMENT OF CHRONIC LUNG DISEASE USING PLURIPOTENT STEM CELLS

FIELD

The present invention relates to a cell preparation in regenerative medicine. More specifically, it relates to an effective cell preparation for treatment of chronic lung disease containing pluripotent stem cells, and to a novel treatment method.

BACKGROUND

Chronic lung disease (CLD), in particular, chronic lung disease in newborns, is a critical complication which occurs at high frequency in newborn medical care, and it is a chronic lung condition recognized from a group of premature babies who have received an artificial ventilation therapy due to respiratory problems like respiratory distress syndrome. Recently, in accordance with a progress in newborn medical care, survival rate of a baby with birth weight of less than 1500 g has increased from less than 70% to 80% or more over last 20 years in many developed countries. However, morbidity of CLD still remains at high rate like 53.2% for a baby of less than 28 weeks of gestation and 40% for a baby with birth weight of less than 1000 g.

With regard to the chronic lung disease in newborns, according to the definition which has been defined internationally in 2001, it is described as "in the case of premature babies of less than 32 weeks of gestation, a baby who requires 21% or higher oxygen therapy for 28 days or longer until 36 weeks after fertilization or before hospital discharge", and the severity is classified based on the oxygen dependency. The chronic lung disease may require home oxygen therapy even after hospital discharge, and it is an important disease from the viewpoint of considering medical economics, for example, hospitalization during childhood due to respiratory infection or the like. Furthermore, decreased respiratory function in chronic lung disease, which affects not only newborns and children but also adolescents, also remains as a huge problem.

It is believed until now that, in chronic lung disease in newborns, damages like infection, patent ductus arteriosus, oxygen toxicity, and artificial ventilation occur in a state in which lung immaturity or surfactant deficiency is present, and, due to the dysplasia of lung tissue, emphysema or fibrosis is caused. However, it is recently considered that the chronic lung disease in newborns is not only a simple damage of lung but also a state in which development of alveoli or vascular system has stopped due to various damages received during the growing process of immature lung at developmental stage after it is released from fetus.

As a therapy for this disease, limiting the concentration of oxygen which is administered as symptomatic therapy, limiting water, reducing water load on pulmonary circulation by using diuretics, administering bronchial dilator or breathing stimulator, or administering steroids in expectation of anti-inflammatory activity or anti-edema activity, and the like are carried out. For example, in Patent Literature 1, to reduce the risk of having newborn chronic lung disease by a patient having respiratory distress syndrome, a pharmaceutical composition applied for intrabronchial administration in which a steroid preparation is combined with a pulmonary surfactant is suggested. However, because the steroid has a risk of a side effect on central nervous system in growth period, it is presently administered, as a rescue measure, in a small amount for a short period time only for severe cases. Namely, for chronic lung disease, the treatment is carried out only as symptomatic therapy, and there has been no report on a pharmaceutical for treatment or a treatment method which aims to achieve complete cure of the disease.

In recent years, while studies based on cell therapy using stem cells are carried out on various diseases and also a clinical application is made in the field of regenerative medicine, it is expected to apply stem cells for the amelioration or treatment of chronic lung disease, for example, bronchopulmonary dysplasia (BPD) (Non Patent Literatures 1 to 3). For example, the bone marrow mesenchymal stem cellular (MSC) fraction is isolated from an adult and is known to have an ability of differentiating into bone, cartilage, adipose cells, nerve cells, skeletal muscle, or the like (Non Patent Literatures 4 and 5). However, MSC is a group of cells in which various kinds of cells are included, the differentiation ability is not entirely clear, and there is a huge variation in therapeutic effect. Furthermore, although iPS cells as pluripotent stem cells derived from an adult have been reported (Patent Literature 2), since iPS cells have a high tumor forming ability in addition to that very complex operations like introducing a specific gene or a specific compound to somatic cells in dermal fibroblast cells as mesenchymal cells is required for establishment of iPS cells, a very high hurdle is present in terms of the clinical application.

Research by Prof. Dezawa, one of the inventors, has demonstrated that the pluripotency of the mesenchymal cells fraction is exhibited by pluripotent stem cells (Multilineage-differentiating Stress Enduring cells, or Muse cells) that express SSEA-3 (Stage-Specific Embryonic Antigen-3) as a surface antigen, which are present in mesenchymal cell fraction and can be obtained without operation of induction and that this holds potential for application in treatment of diseases bytissue regeneration. It has also been found that Muse cells can be enriched by treating the mesenchymal cells fraction with one or more of different types of stress treatments (Patent Literature 3; Non Patent Literature 6). However, it has not yet been demonstrated that the expected therapeutic effect can be obtained using Muse cells for amelioration and/or treatment of chronic lung disease.

CITATION LIST

Patent Literature

[PTL 1] JP 2007-262064 A
[PTL 2] JP 4183742 B1
[PTL 3] WO 2011/007900 A

Non Patent Literature

[NPL 1] Chou, H. C., et al., Am. J. Transl. Res., Vol. 8, p. 342-353 (2016)
[NPL 2] Kim, Y. E., et al., Pediatric Res., 2016, doi: 10.1038/pr. 2016. 88
[NPL 3] Luan, Y., et al., Mol. Med. Rep., Vol. 11, p. 1945-1950 (2015)
[NPL 4] Dezawa, M., et al., J. Clin. Invest., Vol. 113, p. 1701-1710 (2004)
[NPL 5] Dezawa, M., et al., Science, Vol. 309, p. 314-317 (2005)
[NPL 6] Wakao, S, et al., Proc. Natl. Acad. Sci. USA, Vol. 108, p. 9875-9880 (2011)

SUMMARY

Technical Problem

It is an object of the present invention to provide a novel medical use for pluripotent stem cells (i.e., Muse cells) in regenerative medicine. More specifically, it is an object of the present invention is to provide a cell preparation and pharmaceutical composition that include Muse cells and are effective for treatment of chronic lung disease (CLD), as well as a novel treatment method.

Solution to Problem

The present inventors have found that preparing a chronic lung disease rat model, and administering Muse cells by intravenous injection, ameliorates chronic lung disease, and the present invention has thus been completed.

Specifically, the present invention provides as follows.

[1] A cell preparation for amelioration and/or treatment of chronic lung disease, comprising pluripotent stem cells positive for SSEA-3 isolated from mesenchymal tissue of a body or cultured mesenchymal cells.

[2] The cell preparation according to [1] above, comprising a cell fraction wherein the pluripotent stem cells positive for SSEA-3 have been concentrated by external stress treatment.

[3] The cell preparation according to [1] or [2] above, wherein the pluripotent stem cells are CD105-positive.

[4] The cell preparation according to any one of [1] to [3] above, wherein the pluripotent stem cells are CD117-negative and CD146-negative.

[5] The cell preparation according to any one of [1] to [4] above, wherein the pluripotent stem cells are CD117-negative, CD146-negative, NG2-negative, CD34-negative, vWF-negative, and CD271-negative.

[6] The cell preparation according to any one of [1] to [5] above, wherein the pluripotent stem cells are CD34-negative, CD117-negative, CD146-negative, CD271-negative, NG2-negative, vWF-negative, Sox10-negative, Snai1-negative, Slug-negative, Tyrp1-negative, and Dct negative.

[7] The cell preparation according to any one of [1] to [6] above, wherein the pluripotent stem cells have all of the following properties:
  (i) low or non-existent telomerase activity;
  (ii) having the ability to differentiate into any of three germ layers;
  (iii) exhibiting no neoplastic proliferation; and
  (iv) having self-renewal ability.

[8] The cell preparation according to any one of [1] to [7] above, wherein the chronic lung disease is selected from the group consisting of bronchopulmonary dysplasia (BPD), Wilson-Mikity syndrome (WMS), persistent pulmonary hypertension of the newborn (PPHN), and hypertension of the newborn.

[9] The cell preparation according to any one of [1] to [8] above, wherein the pluripotent stem cells have the ability to engraft into lung tissue.

[10] The cell preparation according to any one of [1] to [9] above, which is to be administered to a human newborn, an infant, or a child as a subject with the pluripotent stem cells at from approximately $1 \times 10^4$ cells/individual to approximately $3 \times 10^8$ cells/individual, as a therapeutically effect amount.

[11] The cell preparation according to any one of [1] to [10] above, which is to be administered to a human newborn, an infant, or a child as a subject with the pluripotent stem cells in an amount of cells per body weight of approximately $3 \times 10^4$ cells/kg to approximately $3 \times 10^7$ cells/kg per individual subject, as a therapeutically effect amount.

Advantageous Effects of Invention

According to the present invention, by administering Muse cells via vein or the like to a subject suffering from chronic lung disease (mainly, newborns), an anti-inflammatory activity and a tissue restorative activity are exhibited so that normal lung tissue can be constructed.

BRIEF DESCRIPTION OF DRAWINGS

FIG. 2 illustrates the result of evaluating the lung tissue of a rat model of chronic lung disease belonging to a Muse cell administration group ("Muse"), a group added only with cell suspension (HANK'S BALANCED SALT SOLUTION: HBSS) ("vehicle"), or a sham operation group ("sham"). The short period group has a 15 day old rat as a subject for test, and the long period group has a 29 day old rat as a subject for test. The vertical axis represents the tissue ratio.

FIG. 6 illustrates the result of evaluating heart of a rat model of chronic lung disease belonging to a Muse cell administration group ("Muse group"), a group added only with cell suspension (HBSS) ("vehicle group"), or a sham operation group ("sham group"). The vertical axis represents a value obtained by dividing the weight of the right ventricular wall by the weights of the left ventricular wall and interventricular septum.

FIG. 8 illustrates the result of determining a decrease in thickening of pulmonary arterial vessel wall in various administration groups, in which a change in inner wall ratio of pulmonary arterial vessel is taken as an indicator. FIG. 8(A) is a view in which a tissue having cross-sectional pulmonary arterial vessel is stained by using anti α-SMA antibody. FIG. 8(B) illustrates the result of measuring the inner wall ratio of pulmonary arterial cells both in the short period group and long period group.

FIG. 9 illustrates the result of examining the suppressed neogenesis of pulmonary arterial cells that is augmented in accordance with chronic lung disease in various administration groups.

FIG. 9(A) illustrates the result of histological staining, in which the nucleus of pulmonary arterial cells during proliferation was stained with anti Ki-67 antibody (green), α-smooth muscle actin was stained with anti α-SMA antibody (red), and the nucleus of pulmonary arterial cells was stained with DAPI (blue). FIG. 9(B) illustrates the positive ratio when anti Ki-67 antibody is used.

DESCRIPTION OF EMBODIMENTS

Figure 1:
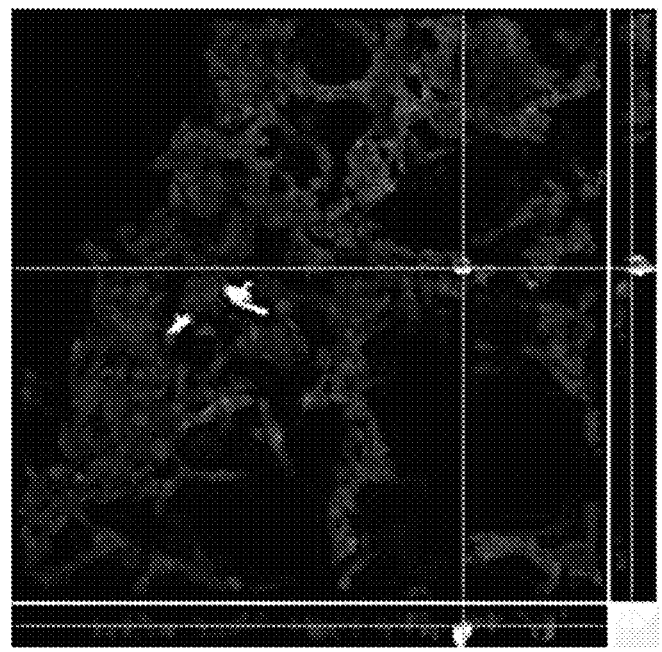
FIG. 1 illustrates the engraftment of GFP-labeled Muse cells in the lung tissue of a 15 day old rat model of chronic lung disease.

The present invention relates to a cell preparation and a pharmaceutical composition for amelioration and/or treatment of chronic lung disease containing SSEA-3-positive pluripotent stem cells (Muse cells), and a novel treatment method. The present invention will now be explained in greater detail.

1. Applicable Diseases and their Diagnosis

The present invention is directed toward amelioration and treatment of chronic lung disease using a cell preparation or pharmaceutical composition containing SSEA-3-positive pluripotent stem cells (Muse cells). In Japan, by the research group of Ministry of Health, Labour and Welfare in 1996, the "chronic lung disorder" in newborns is defined as "due to an anomaly of lung except congenital deformities, respiratory distress symptom requiring oxygen administration starts to occur during newborn period and continues beyond 28 days after birth", and also, to specify a chronic lung disorder of a underweight newborn, which accounts for the most of lung disorder, as a disease, the "chronic lung disease" is defined as a "case with chronic lung disorder which is accompanied by clear abnormal finding like diffuse non-filing defect and bubble-like shade in chest X ray image", and, based on the background factors and chest X ray findings, it is classified into disease types of I to VI as shown in the following Table 1.

Diagnosis of chronic lung disease is made based on a symptom mainly having excessive breathing and chest X ray of respiratory distress syndrome as described in the above criteria. However, exclusive diagnosis after denying the possibility of other respiratory disease serves as a basis.

In general, lung immaturity, oxygen toxicity, artificial ventilation, inflammation, infection, patent ductus arteriosus, and the like are known as a risk factor of chronic lung disease in newborns, and it can be understood as a disease that is caused from a state in which development of alveoli or vascular system is suppressed. However, although not limited thereto, the chronic lung disease as an applicable disease in the present invention may also include bronchopulmonary dysplasia (BPD), Wilson-Mikity syndrome (WMS), persistent pulmonary hypertension of the newborn (PPHN), hypertension of the newborn, and the like. Furthermore, bronchopulmonary dysplasia (BPD) has been firstly reported by Northway et al. in 1967, and, in Western countries, it is generally known as the other name of chronic lung disease.

Chronic lung disease in newborns is a disease largely found in premature babies, and it is a disease with respiratory problem which continuously requires oxygen beyond 28 days after birth or 36 weeks after fertilization. The cause of chronic lung disease is as described in the above, but it is mostly caused by high-oxygen therapy (absorption of high-concentration oxygen for a long period of time, management by high-pressure artificial ventilator, or the like) or inflammation. With regard to infection (inflammation), infection before birth like chorioamnionitis and funisitis becomes a cause of chronic lung disorder, and they can be also an application subject of the present invention. Chorioamnionitis is one of the infections in which infection occurs in amnion, which wraps around a fetus, to cause an infection in placenta. Once chorioamnionitis has occurred, inflammatory substances show a high value inside a fetus, and it is considered, due to that, peeling of epidermis of bronchus or alveoli and a decrease in a material required for regeneration of alveolar structure are caused to yield an onset of chronic lung disorder.

According to the present invention, to treat the above applicable disease, by administering (hereinbelow, it may be also generally referred to as "transplant") to a subject the cell

TABLE 1

Disease classification criteria of chronic lung disease in newborns

I. Chronic lung disorder in newborns preceded by respiratory distress syndrome (RDS) in newborns, in which diffuse bubble-like shade or irregular cord-like or emphysema-like shade is shown in chest X ray image beyond 28 days after birth
II. Chronic lung disorder in newborns preceded by RDS, in which diffuse non-filing defect is shown in chest X ray image beyond 28 days after birth, but there is no bubble-like shade or irregular cord-like or emphysema-like shade
III. Chronic lung disorder in newborns not preceded by RDS, in which infection before birth like high IgM value of umbilical cord blood, chorioamnionitis, funisitis, or the like is highly suspected, and diffuse bubble-like shade or irregular cord-like or emphysema-like shade is shown in chest X ray image beyond 28 days after birth
IV. Chronic lung disorder in newborns not preceded by RDS, in which infection before birth is unclear, but diffuse bubble-like shade or irregular cord-like or emphysema-like shade is shown in chest X ray image beyond 28 days after birth
III'. Chronic lung disorder in newborns not preceded by RDS, in which infection before birth like high IgM value of umbilical cord blood, chorioamnionitis, funisitis, or the like is highly suspected, and diffuse non-filing defect is shown in chest X ray image beyond 28 days after birth, but there is no bubble-like shade or irregular cord-like or emphysema-like shade
V. Chronic lung disorder in newborns not preceded by RDS, in which diffuse non-filing defect is shown in chest X ray image beyond 28 days after birth, but there is no bubble-like shade or irregular cord-like or emphysema-like shade
VI. Case not classified into any of the above I to V preparation and pharmaceutical composition which will be described later, amelioration and/or treatment of the applicable disease can be achieved. As described herein, the "amelioration" means alleviation of various symptoms accompanying the chronic lung disease and suppression of their progress, and it preferably means the alleviation of symptoms to the extent that no significant problem is caused in daily life. Furthermore, the "treatment" indicates suppression or complete removal of various symptoms accompanying the chronic lung disease.

2. Cell Preparation and Pharmaceutical Composition (1) Pluripotent Stem Cells

The pluripotent stem cells to be used in the cell preparation and pharmaceutical composition of the present invention are typically cells whose existence in the human body was discovered by Prof. Dezawa, one of the present inventors, and which are named "Muse (Multilineage-differentiating Stress Enduring) cells". Muse cells can be obtained from bone marrow fluid and adipose tissue (Ogura, F., et al., Stem Cells Dev., Nov. 20, 2013 (Epub) (published on Jan. 17, 2014)) or from skin tissue such as dermal connective tissue, and they are widely dispersed throughout the connective tissue of various organs. The cells have the properties of both pluripotent stem cells and mesenchymal stem cells, and are identified as being double-positive for the cell surface markers "SSEA-3 (Stage-specific embryonic antigen-3)" and "CD105". Therefore, Muse cells or cell populations containing Muse cells, for example, can be isolated from body tissue using these antigen markers. Muse cells are also stress-tolerant, and can be concentrated from mesenchymal tissue or cultured mesenchymal cells by different types of stress treatments. A cell fraction with Muse cells enriched by stress treatment may be used as the cell preparation of the present invention. The methods of separation and identification of Muse cells, and their features, are disclosed in detail in International Patent Publication No. WO2011/007900. Also, as reported by Wakao et al. (2011, ibid.), when mesenchymal cells are cultured from the bone marrow or skin and used as a parent population of Muse cells, all of the SSEA-3 positive cells are also CD105-positive. Consequently, when Muse cells are isolated from mesenchymal tissue of a body or cultured mesenchymal stem cells for the cell preparation and pharmaceutical composition of the present invention, the Muse cells may be used after purification with SSEA-3 alone as the antigen marker. Throughout the present specification, pluripotent stem cells (Muse cells) or a cell population containing Muse cells, isolated from mesenchymal tissue of a body or cultured mesenchymal tissue using SSEA-3 as the antigen marker, and which can be used in a cell preparation and pharmaceutical composition for amelioration and/or treatment of perinatal brain damage, may be referred to simply as "SSEA-3 positive cells". Also throughout the present specification, "non-Muse cells" refers to cells that are present in mesenchymal tissue of a body or cultured mesenchymal tissue, and are the remainder of "SSEA-3 positive cells".

In brief, Muse cells or a cell population containing Muse cells can be isolated from body tissue (for example, mesenchymal tissue) using only antibody for the cell surface marker SSEA-3, or using antibodies for both SSEA-3 and CD105. The term "body" here means "mammalian body". According to the present invention, the "body" does not include a fertilized ovum or an embryo at a developmental stage before the blastocyst stage, but it does include an embryo at the developmental stage from the blastocyst stage onward, including the fetus or blastocyst. The mammal is not limited and may be a primate such as human or monkey, a rodent such as a mouse, rat, rabbit or guinea pig, or a cat, dog, sheep, pig, cow, horse, donkey, goat or ferret. The Muse cells to be used in the cell preparation and pharmaceutical composition of the present invention are clearly distinguished from embryonic stem cells (ES cells) or iPS cells based on separation from body tissue using a direct marker. The term "mesenchymal tissue" refers to tissue from the bone, synovial membrane, fat, blood, bone marrow, skeletal muscle, dermis, ligament, tendon, dental pulp, umbilical cord or umbilical cord blood, or tissues present in various organs. For example, the Muse cells may be obtained from the bone marrow or skin or adipose tissue. Preferably, mesenchymal tissue of a body is harvested and the Muse cells are isolated from the tissue and used. The separating means mentioned above may be used to separate Muse cells from cultured mesenchymal cells such as fibroblasts or bone marrow-derived MSCs. The Muse cells to be used for the cell preparation and pharmaceutical composition of the present invention may be either autologous or allogenic with respect to the recipient.

As mentioned above, Muse cells or a cell population containing Muse cells can be isolated from body tissue using SSEA-3 positivity, or double positivity for SSEA-3 and CD105, as indicators, but human adult skin is known to include various types of stem cells and progenitor cells. However, Muse cells are not identical to these cells. Such stem cells and progenitor cells include skin-derived precursors (SKP), neural crest stem cells (NCSC), melanoblasts (MB), perivascular cells (PC), endothelial precursor cells (EP) and adipose-derived stem cells (ADSC). Muse cells can be separated out as being "non-expressing" for the markers unique to these cells. More specifically, Muse cells can be separated by using non-expression for at least one, and for example, 2, 3, 4, 5, 6, 7, 8, 9, 10 or 11 among 11 markers selected from the group consisting of CD34 (EP and ADSC marker), CD117 (c-kit) (MB marker), CD146 (PC and ADSC marker), CD271 (NGFR) (NCSC marker), NG2 (PC marker), vWF factor (von Willebrand factor) (EP marker), Sox10 (NCSC marker), Snail (SKP marker), Slug (SKP marker), Tyrp1 (MB marker) and Dct (MB marker). As a non-limitative example, non-expression of CD117 and CD146 may be used as the indicator for separation, non-expression of CD117, CD146, NG2, CD34, vWF and CD271 may be used as the indicator, or non-expression of all of the aforementioned 11 markers may be used as the indicator for separation.

The Muse cells having the aforementioned features to be used for the cell preparation and pharmaceutical composition of the present invention may have at least one property selected from the group consisting of the following:
  (i) low or non-existent telomerase activity;
  (ii) having the ability to differentiate into any of the three germ layers;
  (iii) exhibiting no neoplastic prolidration; and
  (iv) having self-renewal ability.

According to one aspect of the present invention, the Muse cells to be used for the cell preparation and pharmaceutical composition of the present invention have all of these properties. As regards (i), "low or non-existent telomerase activity", this refers to low or non-detectable telomerase activity when using a TRAPEZE XL telomerase detection kit (Millipore), for example. "Low" telomerase activity is, for example, either telomerase activity on the same level as human fibroblasts, which are somatic cells, or telomerase activity of $1/5$ and preferably no greater than $1/10$ of that of Hela cells. In regard to (ii), the Muse cells have the ability to differentiate into the three germ layers (endoderm, mesoderm and ectoderm) in vitro and in vivo, and by induction culturing in vitro, for example, they can differentiate into hepatocytes, neurons, skeletal muscle cells, smooth muscle cells, osteocytes or adipocytes. They may also exhibit the ability to differentiate into the three germ layers in the case of transplanting in vivo into the testes. They also have the ability to migrate and engraft onto damaged organs (heart, skin, spine, liver, muscle, etc.), by administration into the body via intravenous injection, and differentiate into specific cells of the corresponding tissue. In regard to (iii), the Muse cells have the property of proliferating at a rate of about every 1.3 days in suspension culture, and growing in suspension culture from a single cell to form an embryoid-like cell mass, slow down the growth at about 14 days; however, when the embryoid-like cell mass is carried into adhesion culture, cell growth resumes and the proliferated cells spread out from the cell mass. They also have the property of not generating teratomas at least for 6 months after transplantation into the testes. In regard to (iv), Muse cells have self-renewal (auto-replicating) ability. The term "self-renewal" means that cells in the embryoid-like cell mass obtained by culturing a single Muse cell in suspension culture can be confirmed to differentiate into cells of all 3 germ layers, and also that when a single cell from the embryoid-like cell mass is again carried into a suspension culture, it forms a next generation embryoid-like cell mass, and reproduce differentiation into three germ layers as well as embryoid-like cell mass in the suspension culture can be confirmed. Self-renewal may be observed once or as several repeated cycles.

In addition, a cell fraction containing Muse cells to be used in the cell preparation of the present invention may be a cell fraction having the SSEA-3 positive and CD105-positive pluripotent stem cells concentrated, obtained by a method of applying external stress treatment to mesenchymal tissue of a body or cultured mesenchymal cells, causing the cells other than the external stress-resistant cells to die, and recovering the surviving cells, the cell fraction having at least one and preferably all of the following properties.

(i) SSEA-3 positivity;
(ii) CD105-positivity;
(iii) low or non-existent telomerase activity;
(iv) having the ability to differentiate into any of the three germ layers;
(v) exhibiting no neoplastic proliferation; and
(vi) having self-renewal ability.

The external stress may be any one or a combination of: protease treatment, culturing in a low oxygen concentration, culturing under low-phosphate conditions, culturing with low serum concentration, culturing under low nutritive conditions, culturing under exposure to heat shock, culturing at low temperature, freezing treatment, culturing in the presence of a hazardous substance, culturing in the presence of active oxygen, culturing under mechanical stimulation, culturing with agitating treatment, culturing with pressure treatment, or physical impact. For example, the treatment time with a protease is preferably a total of 0.5 to 36 hours to apply external stress to the cells. The protease concentration may be the concentration used when the cells adhering to a culture vessel are detached, when the cell mass is dispersed into individual cells, or when individual cells are recovered from tissue. The protease is preferably a serine protease, aspartic acid protease, cysteine protease, metalloprotease, glutamic acid protease or N-terminal threonine protease. The protease is also preferably trypsin, collagenase or dispase.

Muse cells having the aforementioned features, which are to be used in the cell preparation of the present invention, are administered to the body by intravenous administration or the like, after which they engraft onto lung tissue with chronic lung disease, as described below. It is thought that the Muse cells differentiate into tissue-compatible cells thus ameliorating and/or treating chronic lung disease.

(2) Preparation and use of cell preparation and pharmaceutical composition Although not limited thereto, the cell preparation and pharmaceutical composition of the present invention may be obtained by suspending the Muse cells or a cell population containing Muse cells obtained by (1) above, in physiological saline or an appropriate buffer (for example, phosphate-buffered physiological saline, HBSS). In this case, when the number of Muse cells isolated from autologous or allogenic tissue is low, the cells may be cultured before administration for growth until the prescribed cell density is obtained. As already reported (International Patent Publication No. WO2011/007900), Muse cells do not undergo neoplastic transformation, and therefore even if the cells recovered from body tissue are in undifferentiated form, they have low tumorigenicity and are safe. There are no particular restrictions on culturing of the recovered Muse cells, and it may be carried out in ordinary growth medium (for example, α-Minimal Essential Medium (α-MEM) containing 10% newborn calf serum). More specifically, referring to International Patent Publication No. WO2011/007900, suitable medium and additives (for example, antibiotics and serum) may be selected for culturing and growth of the Muse cells, and a solution containing the prescribed density of Muse cells may be prepared. When a cell preparation or pharmaceutical composition of the present invention is to be administered to a human patient, roughly several milliliters of bone marrow fluid may be harvested from human iliac bone, and for example, the bone marrow-derived MSCs may be cultured as adherent cells from the bone marrow fluid to increase them to a number of cells allowing separation of an effective therapeutic amount of Muse cells, after which the Muse cells may be separated out with SSEA-3 antigen marker as the indicator, and autologous or allogenic Muse cells prepared as a cell preparation. As an alternative example, Muse cells that have been separated using SSEA-3 antigen marker as the indicator, and the cells cultured to increase them to an effective therapeutic amount, may then be prepared as a cell preparation of autologous or allogenic Muse cells.

For use of the Muse cells in a cell preparation or pharmaceutical composition, dimethyl sulfoxide (DMSO) or serum albumin may be added to the cell preparation or pharmaceutical composition to protect the cells, and an antibiotic or the like may be added to prevent infiltration and growth of bacteria. In addition, other pharmaceutically acceptable components (for example, carriers, excipients, disintegrators, buffering agents, emulsifying agents, suspending agents, soothing agents, stabilizers, preservatives, antiseptic agents, physiological saline and the like), or cells or components other than Muse cells that are present among MSCs, may be added to the cell preparation or pharmaceutical composition. A person skilled in the art may add such factors and chemical agents to the cell preparation and pharmaceutical composition in appropriate concentrations.

The number of Muse cells in the cell preparation and pharmaceutical composition to be prepared may be appropriately adjusted so as to obtain the desired effect for amelioration and/or treatment of chronic lung disease (for example, lowering the mortality, shortening the days of managing artificial ventilation, and shortening the days of administering oxygen), in consideration of the target gender, age and body weight, the state of the affected area, and the state of the cells to be used. In Examples 2 to 7 below, a rat model of chronic lung disease with high oxygen load was used to examine the effects of transplantation of Muse cells, and in a rat model of approximately 15 to 20 g body weight, a very excellent effect was obtained by administration of SSEA3 positive cells at $1 \times 10^4$ cells/rat (individual). Based on these results, it is expected that for human neonates (within 28 days after birth), infants (less than 1 year after birth) or children (1 to 6 years after birth), administration of cells in an amount of approximately $3 \times 10^4$ cells/kg to approximately $3 \times 10^7$ cells/kg per individual, based on weight, should yield an excellent effect. For example, for a neonate and an infant with a body weight of about 400 to 10,000 g, an estimated dose of about $1 \times 10^4$ cells/individual to about $3 \times 10^8$ cells/individual would be expected to be effective. However, in order to avoid an embolization by administration of cells into blood vessels, the SSEA-3 positive cells may be added to the cell preparation at no greater than $3 \times 10^7$ cells/individual, for example, as the amount per single administration. Here, "individual" includes, but is not limited to, a rat or human.

Furthermore, it is also possible that, till to have a desired therapeutic effect, the cell preparation and pharmaceutical composition of the present invention are administered several times (e.g., 2 to 10 times) with a suitable interval (e.g., twice a day, once a day, twice a week, once a week, or once in 2 weeks). Thus, even though it depends on the state of a subject, the therapeutically effective amount is preferably an administration amount of about $1 \times 10^4$ cells to about $3 \times 10^8$ cells per single individual in 1 to 10 administrations, for example. The total administration amount for single individual can be, although not limited thereto, The cell preparation and pharmaceutical composition of the present invention may be administered several times (for example, 2 to 10 times) at appropriate intervals (for example, twice a day, once a day, twice a week, once a week or once every 2 weeks), until the desired therapeutic effect is obtained. Therefore, the therapeutically effective amount, while depending on the condition of the subject, is preferably a dose of $1 \times 10^4$ cells to $3 \times 10^8$ cells per individual, administered 1 to 10 times, for example. The total amount of administration per individual is not restricted, and may be $1 \times 10^4$ cells to $3 \times 10^9$ cells, $1 \times 10^4$ cells to $1 \times 10^9$ cells, $1 \times 10^4$ cells to $5 \times 10^8$ cells, $1 \times 10^4$ cells to $3 \times 10^8$ cells, $1 \times 10^4$ cells to $1 \times 10^8$ cells, $1 \times 10^4$ cells to $5 \times 10^7$ cells, $1 \times 10^4$ cells to $3 \times 10^7$ cells, $1 \times 10^4$ cells to $1 \times 10^7$ cells, $1 \times 10^4$ cells to $5 \times 10^6$ cells, $1 \times 10^4$ cells to $3 \times 10^6$ cells, $1 \times 10^4$ cells to $1 \times 10^6$ cells, $1 \times 10^4$ cells to $5 \times 10^5$ cells, $1 \times 10^4$ cells to $3 \times 10^5$ cells, $1 \times 10^4$ cells to $1 \times 10^5$ cells, $1 \times 10^5$ cells to $3 \times 10^9$ cells, $1 \times 10^5$ cells to $1 \times 10^9$ cells, $1 \times 10^5$ cells to $5 \times 10^8$ cells, $1 \times 10^5$ cells to $3 \times 10^8$ cells, $1 \times 10^5$ cells to $1 \times 10^8$ cells, $1 \times 10^5$ cells to $5 \times 10^7$ cells, $1 \times 10^5$ cells to $3 \times 10^7$ cells, $1 \times 10^5$ cells to $1 \times 10^7$ cells, $1 \times 10^5$ cells to $5 \times 10^6$ cells, $1 \times 10^5$ cells to $3 \times 10^6$ cells, $1 \times 10^5$ cells to $1 \times 10^6$ cells, $1 \times 10^6$ cells to $3 \times 10^9$ cells, $1 \times 10^6$ cells to $1 \times 10^9$ cells, $1 \times 10^6$ cells to $5 \times 10^8$ cells, $1 \times 10^6$ cells to $3 \times 10^8$ cells, $1 \times 10^6$ cells to $1 \times 10^8$ cells, $1 \times 10^6$ cells to $5 \times 10^7$ cells, $1 \times 10^6$ cells to $3 \times 10^7$ cells, $1 \times 10^6$ cells to $1 \times 10^7$ cells, $1 \times 10^6$ cells to $3 \times 10^9$ cells, $1 \times 10^7$ cells to $1 \times 10^9$ cells, $1 \times 10^7$ cells to $5 \times 10^8$ cells, $1 \times 10^7$ cells to $3 \times 10^8$ cells, $1 \times 10^7$ cells to $1 \times 10^8$ cells, $1 \times 10^5$ cells to $3 \times 10^8$ cells, $1 \times 10^5$ cells to $1 \times 10^8$ cells, $1 \times 10^5$ cells to $5 \times 10^7$ cells, $1 \times 10^5$ cells to $3 \times 10^7$ cells, $1 \times 10^5$ cells to $1 \times 10^7$ cells, $1 \times 10^5$ cells to $5 \times 10^6$ cells, $1 \times 10^5$ cells to $3 \times 10^6$ cells, $1 \times 10^5$ cells to $1 \times 10^6$ cells, $5 \times 10^5$ cells to $3 \times 10^8$ cells, $5 \times 10^5$ cells to $1 \times 10^8$ cells, $5 \times 10^5$ cells to $5 \times 10^7$ cells, $5 \times 10^5$ cells to $3 \times 10^7$ cells, $5 \times 10^5$ cells to $1 \times 10^7$ cells, $5 \times 10^5$ cells to $5 \times 10^6$ cells, $5 \times 10^5$ cells to $1 \times 10^6$ cells, $1 \times 10^6$ cells to $1 \times 10^8$ cells, $1 \times 10^6$ cells to $5 \times 10^7$ cells, $1 \times 10^6$ cells to $1 \times 10^7$ cells, $1 \times 10^6$ cells to $5 \times 10^6$, or the like.

Although the cell preparation and pharmaceutical composition of the present invention have chronic lung disease as a subject for the amelioration and treatment, the time for administration is after having diagnosis of chronic lung disease according to pediatric findings, chest Roentgen image, CT or the like after birth, and it can be also within several months immediately after the diagnosis. Alternatively, even at early stage after birth, it can be the time at which high possibility of having chronic lung disease is recognized due to poor breathing state (e.g., 1 week after birth). Meanwhile, according to the present invention, the cell preparation or the like is preferably administered immediately after having the disease, but, even at later time after having the disease, e.g., 1 week, 1 month, 3 months, 6 months, or 12 months after having the disease, it is possible to have the effect of the cell preparation of the present invention. Furthermore, as it has been confirmed according to the experiment by the inventors of the present invention that Muse cells to be used do not cause an immune response even in a case in which they have an allogenic origin, they can be suitably administered till to have the effect that is desired by the amelioration and treatment of chronic lung disease. Furthermore, as shown in Examples 2 to 7 that will be described later, when evaluation of the lung tissue and evaluation of heart are carried out with regard to the amelioration of the disease by Muse cells using a rat model of chronic lung disease, it was found that the long period (29 days after birth) therapeutic effect tends to be more significant than the short period (15 days after birth) therapeutic effect.

3. Preparation of Rat Model of Chronic Lung Disease

In the present specification, in order to determine the effect of ameliorating and treating chronic lung disease by the cell preparation of the present invention, a rat model of chronic lung disease can be established and used. As for the rat to be used as a model, Wistar/ST strain rat and Sprague Dawley (SD) strain rat can be generally mentioned, although it is not limited thereto. The method for preparing a rat model of chronic lung disease is well known, and a rat model of chronic lung disease can be prepared according to the method of Lu, A. et al., (Pediatr. Res., 77, 784-792 (2015)). Furthermore, according to an evaluation of the lung tissue, an occurrence of chronic lung disease in a rat model, which has been prepared by the above method, can be determined.

Muse cells that are used for the cell preparation and pharmaceutical composition of the present invention have a property of integrating in a disease part. Accordingly, with regard to administration of the cell preparation or pharmaceutical composition, the administration site (e.g., intraperitoneal, intramuscular, disease part), type of blood vessels for their administration (vein or artery), and the like are not limited. Furthermore, as a method for confirming the engraftment of administered Muse cell after their arrival to a disease part, by preparing in advance Muse cell having incorporated gene to express a fluorescent protein (e.g., green fluorescent protein (GFP)) and, after administering to a body, observing by a method for detecting fluorescence (e.g., immunohistostaining), behavior of Muse cells can be determined. Furthermore, since Muse cells used for the cell preparation and pharmaceutical composition of the present invention are derived from human, they are in heterogeneous relationship with rat. In an experiment in which heterogeneous cells or the like are administered to a model animal, to suppress the rejection to heterogeneous cells in a body, an immunosuppressive agent (cyclosporin or the like) can be administered before or simultaneously with the administration of heterogeneous cells.

4. Effect of Amelioration and Treatment by Muse Cells in Rat Model of Chronic Lung Disease In an embodiment of the present invention, the cell preparation and pharmaceutical composition of the present invention can ameliorate and/or treat chronic lung disease and various accompanying symptoms in mammals including human. According to the present invention, by using the rat model of chronic lung disease prepared in the above and experimentally determining amelioration or the like of symptoms in a rat having chronic lung disease by Muse cells, the effect of Muse cells can be evaluated. As the evaluation method, a general measurement system for evaluating pulmonary function using rat can be used, and, for example, a system for evaluating breathing and pulmonary function of a rat like FinePointe (trademark)-Noninvasive Airway Mechanics (NAM) as a system for evaluating breathing and pulmonary function can be used. Furthermore, evaluation can be made by measuring alveolar wall (enlarged cavity between alveoli), measuring mRNA expression amount of inflammatory cytokines or the like, evaluating right ventricular muscle relating to chronic lung disease, or evaluating pulmonary blood vessels for the lung tissue that are collected from a rat model.

(1) Evaluation of Lung Tissue

According to the present invention, as one of the evaluations of the lung tissue, the effect of improving a treatment of chronic lung disease can be evaluated by measuring tissue volume density. Simply, the lung tissue collected from a test subject are fixed with 4% paraformaldehyde, and a paraffin block section is prepared and stained with hematoxylin and eosin. By counting the ratio of the lung tissue in the predetermined number of grids under a microscope, lesions of the lung tissue can be evaluated (see Example 4 which will be described later). If there is a damage in the lung tissue, high alveolar cavity ratio is expected.

In another embodiment, by measuring an expression amount of inflammatory cytokines that are expressed in the lung tissue, effectiveness of the cell preparation or pharmaceutical composition of the present invention for chronic lung disease can be evaluated. In general, IL-1α, IL-1β, IL-6, CCL2 (MCP-1), TNF-α, TGF-β, VEGF, or the like are exemplified as an inflammatory cytokine. The expression amount of inflammatory cytokines that are expressed in the tissue can be measured by a common method, for example, by using RT-PCR. As it is described in Example 5 which will be described later, compared to a control group administered with a vehicle, the expression amount of inflammatory cytokines can be significantly reduced in a group administered with Muse cells, and thus Muse cells are expected to be useful for a treatment of chronic lung disease.

(2) Evaluation of Heart (Evaluation of Pulmonary Hypertension)

In chronic lung disease caused by high oxygen load, thickening of pulmonary blood vessels occurs due to the applied high oxygen concentration, and thickening of heart is found in accordance with it. Chronic lung disease in newborns accompanies secondary pulmonary hypertension (as the disease becomes more severe). This secondary pulmonary hypertension is also an important factor which decides the life prognosis. Because continuous pulmonary hypertension leads to thickening of right ventricular wall caused by right cardiac load, pulmonary hypertension can be also evaluated by utilizing an evaluation of heart (cardiac muscle). As it is described in Example 6 which will be described later, also in the rat model of chronic lung disease, thickening of right ventricular wall which is considered to be caused by right cardiac load is observed, and this thickening can be reduced by administration of Muse cells.

(3) Measurement of Number of Inflammatory Cells in Alveolar Lavage Fluid

An increase in the number of inflammatory cells is observed in chronic lung disease. The therapeutic effect for chronic lung disease by various treatments can be evaluated by measuring the number of inflammatory cells in alveolar lavage fluid. As it is described in Example 7 which will be described later, Muse cells can reduce in a significant sense the number of inflammatory cells in a rat model of chronic lung disease.

The present invention will now be explained in more specific detail through the following examples, with the understanding that the present invention is in no way limited by the examples.

EXAMPLES

Example 1: Preparation of Muse Cells

Muse cells were obtained based on the method described in WO 2011/007900 A which relates to isolation and identification of human Muse cells.

Example 2: Preparation of Rat Model of Chronic Lung Disease and Administration of Muse Cells Protocols relating to the test animals used in the present research were approved by Animal Test Committee of Medical School, Nagoya University. A pregnant SD rat was obtained from Japan SLC, Inc. (Shizuoka, Japan). Immediately after birth (within 24 hours), a mother rat and a baby rat were allowed to have free access to food and water during the test period, and kept in a cage applied with high oxygen load (animal chamber provided with oxygen controller and sensor adaptor) under 12-hour light and dark cycle. The animal chamber and inside of the cage were constantly maintained at 23° C. Because the mother rat also suffers from high oxygen condition, replacement with a surrogate mother was carried out every 2 days.

A 5 day old rat model of chronic lung disease was anesthetized by isoflurane inspiration, and, for the treatment group, Muse cells ($1 \times 10^4$ cells/individual) were administered through right external jugular vein (treatment group). For the control group, only HBSS in the same volume as Muse cells was administered instead of Muse cells. A rat not provided with any of Muse cells and HBSS and also not applied with high oxygen was employed as a sham group. In the following experiments, 15 day old rats and 29 day old rats were taken as a short period group and a long period group, respectively, and used for various evaluations. Furthermore, rats were exposed to high oxygen concentration (80%) till to day 15 for which the short period evaluation is carried out, and, after that, the rats were exposed to common oxygen concentration (21%) till to day 29 for which the long period evaluation is carried out.

Example 3: Confirmation of Engraftment of Muse Cells in Lung Tissue

An experiment for confirming engraftment of Muse cells, which have been used for the transplant, in the lung tissue was carried out. First, to express the green fluorescent protein (GFP) and have Muse cells get labeled with it, lentivirus-GFP gene was introduced in advance to Muse cells. By FACS, GFP-labeled Muse cells were isolated as GFP and SSEA-3 double positive cells. After that, as described in Example 2, Muse cells were administered.

Next, from the lung of a 15 day old rat administered with Muse cells (on day 14 after applying high oxygen), engraftment of Muse cells in the lung tissue was confirmed as follows. After sacrificing the rat, the lung was cut and a section of the lung tissue was prepared by a common method. By preparing a freeze-dried section, antigen retrieval was carried out by using HistoVT one (NACALAI TESQUE, INC.). To prevent the non-specific binding of an antibody, blocking was carried out by using donkey blood serum. After that, incubation with anti GFP antibody was carried out overnight at 4° C. Subsequently, additional incubation was carried out using a suitable secondary antibody. After that, mounting was carried out using a mounting medium which contains DAPI for staining DNA. From the result, it was shown that Muse cells transplanted through right external jugular vein of the rat engraft in the lung tissue having lung disorder (FIG. 1).

Example 4: Evaluation of Lung Tissue

Evaluation of the lung tissue of a rat model of chronic lung disease was carried out as follows. The rat model belonging to the above short period group or long period group was sacrificed. After perfusing pulmonary vessels by injecting physiological saline from right ventricle, the lung was expanded with 4% aqueous paraformaldehyde solution through bronchial catheter (20 cm $H_2O$, for 20 minutes). The lung was removed and fixed for 18 to 24 hours (4° C.) in a 4% paraformaldehyde solution, and then cut and divided into each lung lobe. Cut and divided lung lobes were dehydrated with aqueous ethanol solution and xylene, and, after paraffin embedding, the lung lobes were prepared as a section with thickness of 5 μm. According to hematoxylin-eosin staining (HE staining), a sample was prepared. By using an inverted microscope (Model No. IX83, manufactured by Olympus Corporation), 100 grids (×3 areas×6 sections) were placed over a microscope software (Stereo Investigator), and determination was made to examine the area under each grid, whether the area is a space or a lung tissue. The evaluation was made to determine the percentage (%) of the lung tissue in 100 grids (1,800 in total). In normal lung tissue, alveolar cavity corresponds to 40% or so in general, and alveolar cavity increases in accordance with a damage occurring in the lung tissue. As illustrated in FIG. 2, for the rats of short treatment group (15 day old), the treatment group administered with Muse cells (Muse group) and the treatment group administered with HBSS (vehicle group) showed the same level as the sham group in normal state. However, in the rat of long period group (29 day old), a significant effect is exhibited from Muse group compared to the vehicle group, and alleviation close to the normal state was shown.

Figure 3:
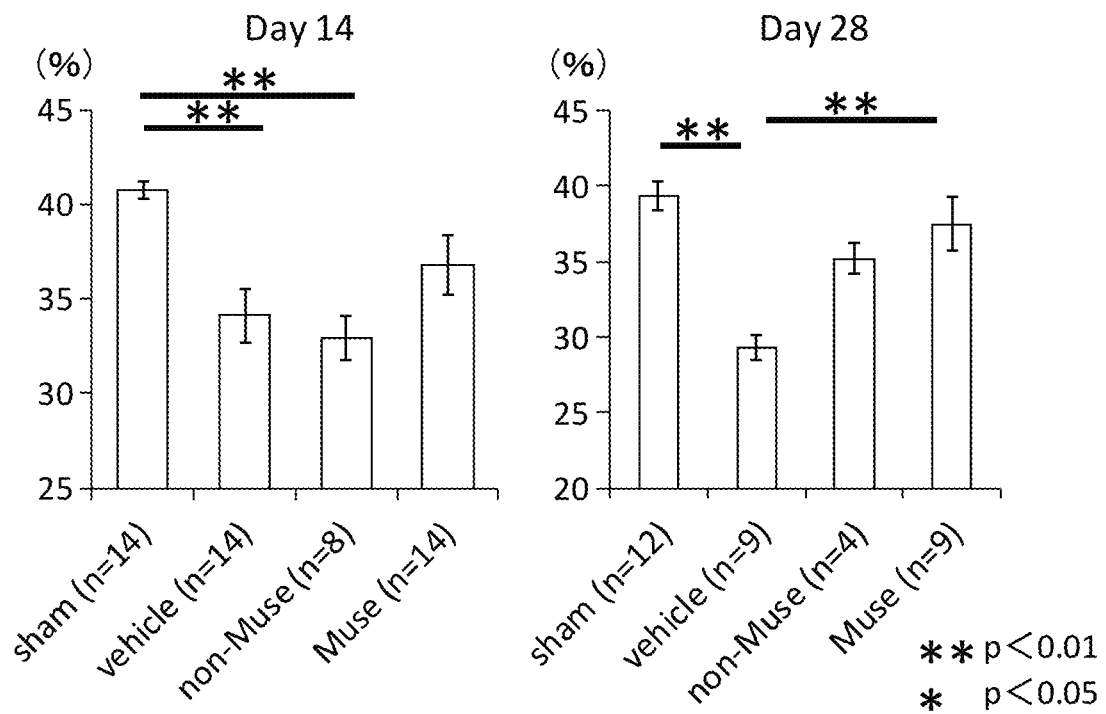
FIG. 3 illustrates the result of evaluating the lung tissue of a rat model of chronic lung disease belonging to a Muse cell administration group ("Muse"), a non Muse cell administration group ("non Muse"), a group added only with cell suspension (HBSS) ("vehicle"), or a sham operation group ("sham"). The short period group has a 15 day old rat as a subject for test, and the long period group has a 29 day old rat as a subject for test. The vertical axis represents the tissue ratio.

Similar to above, other than the group newly administered with Muse cells, vehicle group, and sham group, a group administered with non Muse cells was added, and the lung tissue from the rats of short period group and long period group were evaluated again (FIG. 3). In the short period group, the treatment group administered with non Muse cells (non Muse group) was at the same level as the vehicle group and it was not observed with any effect of reducing a damage in the lung tissue. However, from the group administered with Muse cells (Muse group), the effect of significantly reducing a damage in the lung tissue by Muse cells was observed like the previous result (FIG. 2). Meanwhile, in the long period group, the effect of reducing a damage in the lung tissue was observed from the non Muse group when compared to the vehicle group. However, the effect was small compared to the Muse group. From the rats administered with Muse cells, it was shown that, like the previous result, the damage in the lung tissue is alleviated close to the normal state.

Furthermore, by measuring the alveolar wall ratio of a 29 day old rat, evaluation of the lung tissue was carried out. Prepared sample was photographed by a digital camera for microscope (Model No. DP73, manufactured by Olympus Corporation). Photographed image was analyzed by using an imaging software (trade name: cellSens, manufactured by Olympus Corporation). Alveolar area was obtained by subtracting the areas of organs, blood vessels, and disorder part from the whole area of a sample section, and, in the alveolar area, ratio of the area taken by alveolar wall (alveolar wall ratio) was calculated based on the following equation.

$$\text{Alveolar wall ratio (\%)} = \text{Alveolar wall area} \div \{\text{Whole area of lung sample} - (\text{Area of organ part} + \text{Area of blood vessel part} + \text{Area of disorder part})\} \times 100$$

Figure 4:
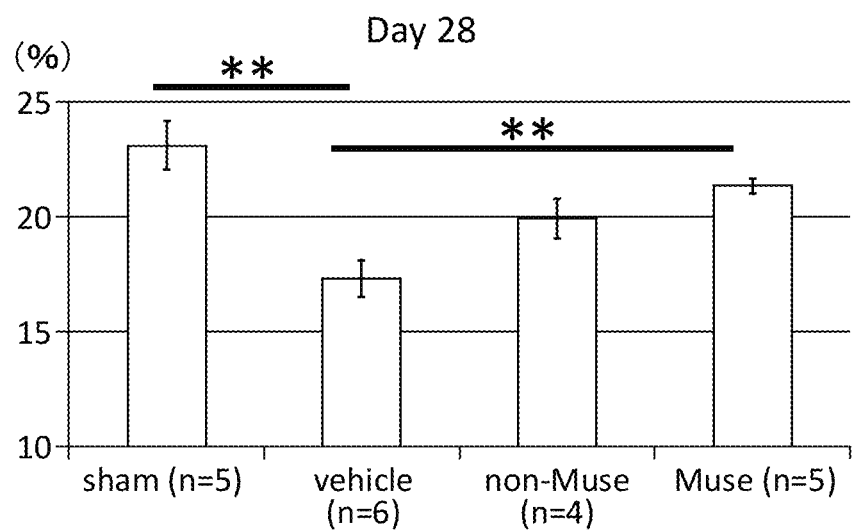
FIG. 4 illustrates the result of evaluating alveolar wall ratio in the lung tissue of a 29 day old rat. Higher alveolar wall ratio indicates denser forming of alveolar wall, showing restoration of the lung tissue.

Higher alveolar wall ratio indicates denser forming of alveolar wall to have restored the lung tissue. The results are shown in FIG. 4. In the sham group, the alveolar wall ratio was about 22 to 23%, and in the group in which the rat model of chronic lung disease is administered with Muse cells, disrupted alveolar wall was recovered to 21% or so. Furthermore, although the recovering effect was also shown from the non Muse cell group, the effect was not as high as the Muse cell group. Accordingly, from the above evaluation of the lung tissue, it was shown that a significant effect is shown in the lung Muse group and alleviation close to the normal state is exhibited.

Example 5: Measurement of mRNA Expression of Inflammatory Cytokines

Figure 5:
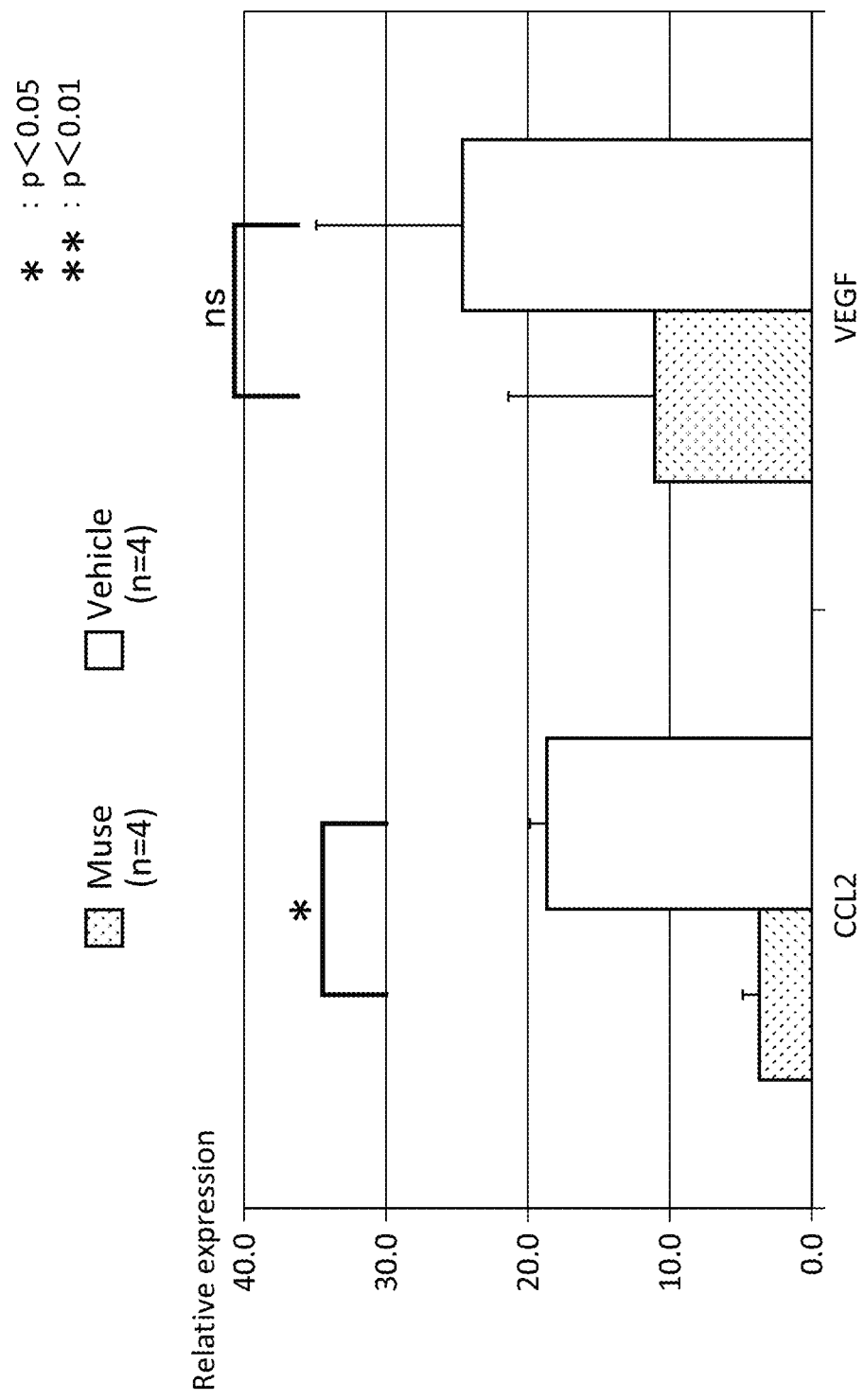
FIG. 5 illustrates the result of measuring the mRNA expression amount of inflammatory cytokines that are expressed in the lung tissue of a 15 day old rat model of chronic lung disease. The vertical axis represents the relative expression amount when the sham operation group is set at 1.

In chronic lung disease, expression of various inflammatory cytokines is increased in the lung tissue, and determination was made to see as to whether or not their expression amount can be reduced by transplant of Muse cells. From a 15 day old rat, the lung tissue were collected, and RNA was extracted by a common method. After that, expression amount of mRNA of CCL2 and VEGF, which are inflammatory cytokines, was compared between the treatment group and vehicle group. As a specific technique, TRI reagent was added to a vessel in which the lung tissue have been quickly collected, and homogenization was carried out using Dounce homogenizer and a syringe with 21 G needle. After adding chloroform, an aqueous layer containing RNA was obtained by centrifuge. RNA was precipitated with isopropanol, and RNA dissolved to designated concentration was used for synthesis of cDNA using SuperScript (registered trademark) VILO (trademark) cDNA Synthesis Kit. After that, real time quantitative RT-PCR was carried out by using SYBR Green. The results are shown in FIG. 5. The vertical axis represents the relative expression amount of mRNA of each cytokine when the expression amount of the sham group is set at 1. Compared to the treatment group administered with HBSS (vehicle group), the treatment group administered with Muse cells (Muse group) can have mRNA expression amount of any kind of inflammatory cytokines that is reduced in significant sense.

Example 6: Evaluation of Heart (Evaluation of Pulmonary Hypertension)

With regard to the therapeutic effect of Muse cells on chronic lung disease, an evaluation using heart of a rat was carried out. From the rat models of the above short period group and long period group, heart was collected and divided into two parts, right ventricular wall (RV) and interventricular septum+left ventricular wall (IVS+LV). According to sufficient drying using a dryer (for 48 hours at 60° C.), weight was measured for each of them. When there is continuous pulmonary hypertension, right ventricular wall is thickened (gets heavier). The sham group of FIG. 6 shows a normal value, but with chronic lung disease (vehicle group), the value has increased to 0.4 or so. This indicates the thickening of right ventricle. On the other hand, it was recognized that the group administered with Muse cells (Muse group) exhibits almost the normal state.

Figure 7:
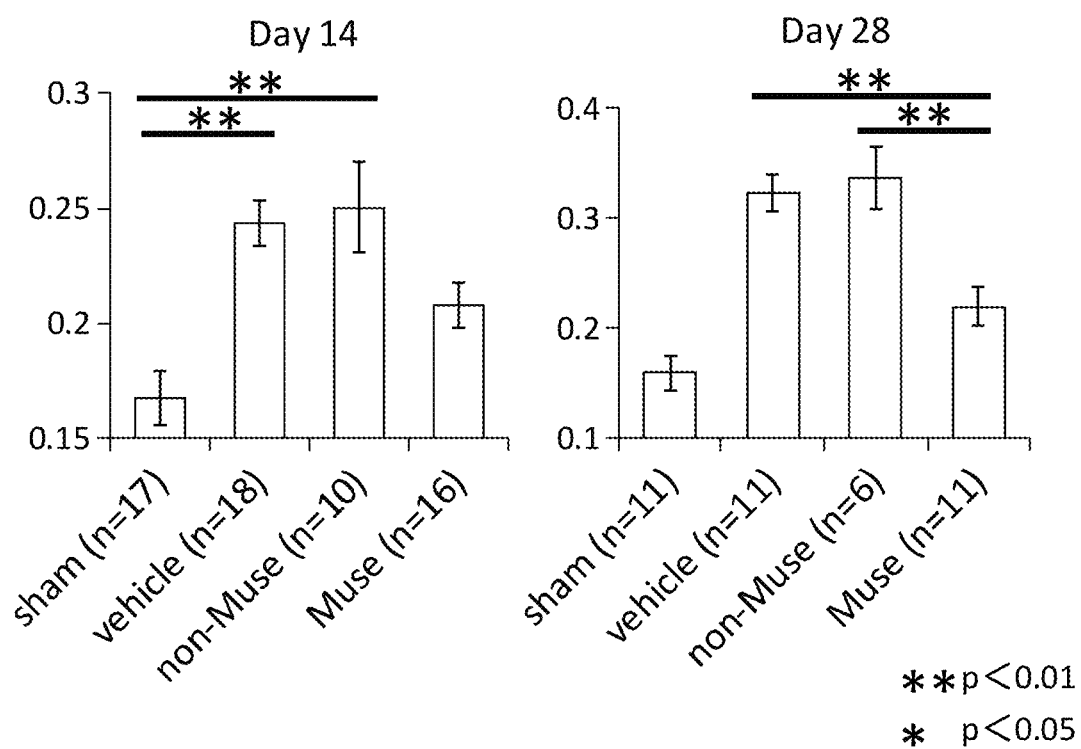
FIG. 7 illustrates the result of evaluating heart of a rat model of chronic lung disease belonging to a Muse cell administration group ("Muse group"), a non Muse cell administration group ("non Muse cells"), a group added only with cell suspension (HBSS) ("vehicle group"), or a sham operation group ("sham group"). The vertical axis represents a value obtained by dividing the weight of the right ventricular wall by the weights of the left ventricular wall and interventricular septum.

Similar to above, other than the group newly administered with Muse cells, vehicle group, and sham group, a group administered with non Muse cells was added, and the effect of ameliorating lung hypertension in the rats of short period group and long period group was evaluated again (FIG. 7). In both the short period group and long period group, the treatment group administered with non Muse cells (non Muse group) was at the same level as the vehicle group and it was not observed with any effect of reducing the pulmonary hypertension. However, from the group administered with Muse cells (Muse group), the effect of significantly reducing the pulmonary hypertension by Muse cells was observed like the previous result (FIG. 6).

Subsequently, with regard to the restoration of the lung tissue which have been damaged by high oxygen load, histological evaluation was carried out. Initially, the blood vessel wall of pulmonary artery was histologically stained using anti α-SMA (α-smooth muscle actin) antibody, and, for each administration group, the effect of reducing the thickening of pulmonary artery wall was evaluated by having a change in inner wall ratio as an indicator. At the same time, to see whether or not the neogenesis of pulmonary arterial cells, which is augmented in accordance with chronic lung disease, can be suppressed by administration of Muse cells, determination was made by using Ki-67, which is a nuclear protein relating to cell cycle, as a cell proliferation marker. Similar to the above example, a paraffin section was prepared, and antigen retrieval was carried out with citric acid buffer. To prevent the non-specific binding of an antibody, blocking was carried out by using donkey blood serum. After that, incubation with anti α-SMA antibody and anti Ki-67 antibody was carried out overnight at 4° C. After carrying out additional incubation using a suitable secondary antibody, mounting was carried out using a mounting medium which contains DAPI for staining DNA.

The result of histological staining in cross-section of pulmonary artery blood vessel is shown in FIG. 8(A). Based on those images, inner wall ratio of each group was calculated based on the following equation, and the results are shown in FIG. 8(B):

Inner wall ratio (%)={(Outer diameter of blood vessel−Inner diameter of blood vessel)/Outer diameter of blood vessel}×100

As it is shown in the view, a similar result was shown from both of the short period group and long period group, and the thickening of pulmonary artery blood vessel wall caused by pulmonary hypertension was significantly suppressed in the Muse cell group. Furthermore, although the suppressive effect is also observed from the non Muse cell group, the effect was smaller compared to the Muse cell group.

Nucleus of the pulmonary arterial cells during proliferation was subjected to histological staining using anti Ki-67 antibody and neogenesis rate of the pulmonary arterial cells was evaluated. In FIG. 9(A), the result of carrying out triple staining using anti α-SMA antibody, anti Ki-67 antibody, and DAPI was shown. The pulmonary artery sample shown in the view belongs to a group administered with non Muse cells, and pulmonary arterial cells during proliferation, which have been stained with anti Ki-67 antibody, were observed therefrom.

Next, the above triple staining was carried out for each group, and ratio of Ki-67 positive cells in pulmonary arterial cells of which nucleus has been stained by DAPI was calculated (FIG. 9(B)). In the short period group, neogenesis of the pulmonary arterial cells in the Muse cell group showed decreased ratio of Ki-67 positive cells compared to the vehicle group and the non Muse cell group. Furthermore, in the long period group, the Muse cell group showed decreased ratio of Ki-67 positive cells, which is identical to the sham group, and the effect was more significant than the short period group. From the above evaluation of pulmonary hypertension, it was shown that Muse cells exhibit a significant effect in a treatment of chronic lung disease.

Figure 10:
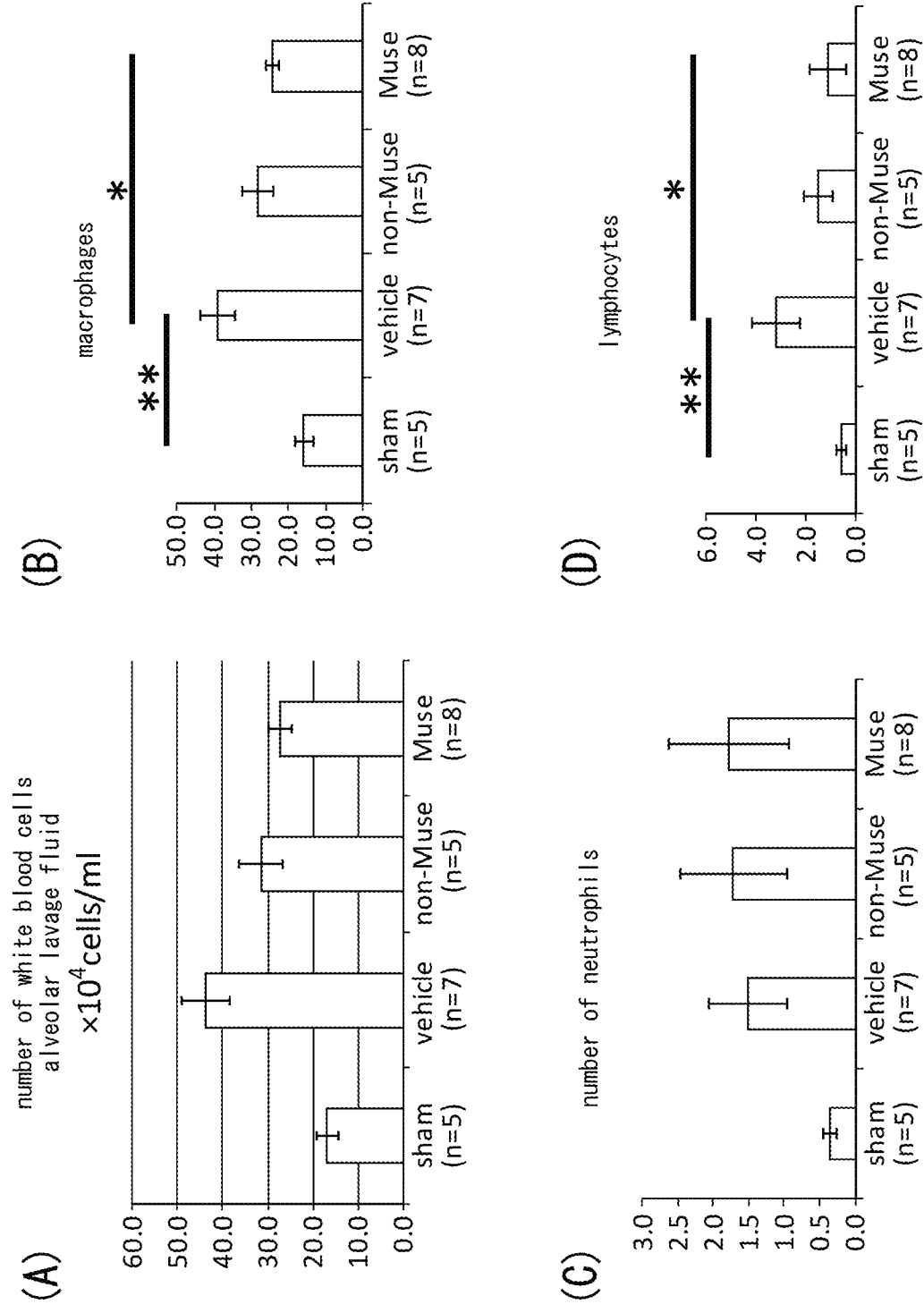
FIG. 10 illustrates the result of examining the number of inflammatory cells in alveolar lavage fluid.

Example 7: Measurement of Number of Inflammatory Cells in Alveolar Lavage Fluid The increase in the number of inflammatory cytokines is observed from chronic lung disease. In this regard, determination was made to see whether or not the number of these cells is reduced by administration of Muse cells. After sacrificing rats of the short period group, blood vessel was perfused through pulmonary artery with physiological saline. By injecting 0.4 ml of physiological saline (0.2 ml×2 times) using intubated bronchial cannula, bronchoalveolar lavage (BAL) was carried out and BAL fluid (BALF) was collected. The number of the white blood cells, macrophages, neutrophils, and lymphocytes in BALF was measured according to the following technique. Specifically, to 10 μL of bronchoalveolar lavage fluid, 20 μL of Turk solution was added for staining, and, by using Burker-Turk hemocytometer, total cell number was counted. Subsequently, by using Cytospin4 (registered trademark), slide sample having 100 μL of bronchoalveolar lavage fluid was prepared, and the prepared slide sample was stained by May-Giemsa staining. By counting at least 200 cells per sample under a microscope, the white blood cell fraction was measured, and the number of macrophages, the number of neutrophils, and the number of lymphocytes were calculated. The results are shown in FIG. 10. The number of various inflammatory cells, which have increased in accordance with chronic lung disease, was reduced by the administration of Muse cells. From this result, it was shown that Muse cells exhibit a significant effect in a treatment of chronic lung disease.

INDUSTRIAL APPLICABILITY

The cell preparation and pharmaceutical composition of the present invention can be applied for amelioration and treatment of chronic lung disease in newborns.

All of the publications and patent literature cited herein are incorporated into the present specification in their entirety as reference. The specific embodiments of the present invention were explained in the present specification for the purpose of example, and it will be easily appreciated by a person skilled in the art that various modifications may be employed such as are not outside of the spirit and scope of the present invention.

The invention claimed is:

1. A method of treating persistent pulmonary hypertension of the human newborn (PPHN) and/or hypertension of the human newborn caused by chronic lung disease, the method comprising:
   (i) intravenously administering a therapeutically effective amount of human pluripotent stem cells to a human newborn that has PPHN and/or hypertension of the human newborn caused by chronic lung disease,
      wherein the human pluripotent stem cells are isolated from mesenchymal tissue, and
      wherein the human pluripotent stem cells express SSEA-3 and CD105 but do not express CD117 and CD146, have low or no telomerase activity; have the capability to differentiate into any of three germ layers; exhibit no neoplastic proliferation; and have ability to self-renewal.

2. The method according to claim 1, wherein the human pluripotent stem cells positive for SSEA-3 have been concentrated by external stress treatment.

3. The method according to claim 1, wherein the human pluripotent stem cells are CD117-negative, CD146-negative, NG2-negative, CD34-negative, vWF-negative, and CD271-negative.

4. The method according to claim 1, wherein the human pluripotent stem cells are CD34-negative, CD117-negative, CD146-negative, CD271-negative, NG2-negative, vWF-negative, Sox10-negative, Snail-negative, Slug-negative, Tyrp1-negative, and Dct negative.

5. The method according to claim 1, wherein the therapeutically effective amount of human pluripotent stem cells is from approximately $1 \times 10^4$ cells/individual to approximately $3 \times 10^8$ cells/individual.

6. The method according to claim 1, wherein the therapeutically effective amount of human pluripotent stem cells is approximately $3 \times 10^4$ cells/kg to approximately $3 \times 10^7$ cells/kg per individual subject.

* * * * *